(12) United States Patent
Peng et al.

(10) Patent No.: US 12,670,593 B2
(45) Date of Patent: Jun. 30, 2026

(54) IDENTIFYING AND QUANTIZING SYSTEM, OPERATION METHOD THEREOF, AND NON-TRANSITORY COMPUTER READABLE MEDIUM

(71) Applicants: Taipei Medical University (TMU), Taipei City (TW); Taipei Veterans General Hospital, Taipei City (TW)

(72) Inventors: Syu-Jyun Peng, Zhubei City (TW); Chi-Jen Chou, Kaohsiung City (TW); Huai-Che Yang, Taipei City (TW)

(73) Assignees: Taipei Medical University (TMU), Taipei City (TW); Taipei Veterans General Hospital, Taipei City (TW)

( * ) Notice: Subject to any disclaimer, the term of this patent is extended or adjusted under 35 U.S.C. 154(b) by 239 days.

(21) Appl. No.: 18/625,661

(22) Filed: Apr. 3, 2024

(65) Prior Publication Data

US 2025/0111503 A1 Apr. 3, 2025

(30) Foreign Application Priority Data

Oct. 3, 2023 (TW) .................................. 112137958

(51) Int. Cl.
| | |
|---|---|
| *G06T 7/00* | (2017.01) |
| *G06T 7/11* | (2017.01) |
| *G16H 30/40* | (2018.01) |

(52) U.S. Cl.
CPC .............. *G06T 7/0012* (2013.01); *G06T 7/11* (2017.01); *G16H 30/40* (2018.01); *G06T 2207/10088* (2013.01); *G06T 2207/20081* (2013.01); *G06T 2207/20084* (2013.01); *G06T 2207/30016* (2013.01); *G06T 2207/30096* (2013.01)

(58) Field of Classification Search
CPC ..................... G06T 7/0012; G06T 7/11; G06T 2207/10088; G06T 2207/20081; G06T 2207/20084; G06T 2207/30016; G06T 2207/30096; G16H 30/40
See application file for complete search history.

(56) References Cited

U.S. PATENT DOCUMENTS

| | | | |
|---|---|---|---|
| 8,163,494 | B2 | 4/2012 | Neufeld |
| 8,754,124 | B2 | 6/2014 | Ahn et al. |

(Continued)

FOREIGN PATENT DOCUMENTS

| | | |
|---|---|---|
| CN | 2910255 Y | 6/2007 |
| CN | 101015723 A | 8/2007 |

(Continued)

*Primary Examiner* — Gregory M Desire

(57) ABSTRACT

The present disclosure provides an operating method of an identifying and quantizing system, which includes steps as follows. The T2 weighted image is split into a first group of two-dimensional images; the first group of two-dimensional images is inputted into the mask R-CNN model to obtain the first group of two-dimensional parenchymal brain images; a first group of two-dimensional parenchymal brain images is used to form T2 weighted parenchymal brain images; T2 weighted parenchymal brain image is pre-processed to obtain a pre-processed T2 weighted parenchymal brain image; a three-dimensional convolutional neural network model is used to segment and quantize the brain edema area in the pre-processed T2 weighted parenchymal brain image.

12 Claims, 2 Drawing Sheets

(56) References Cited

U.S. PATENT DOCUMENTS

| | | | |
|---|---|---|---|
| 9,053,534 B2 | 6/2015 | Ross et al. | |
| 9,321,737 B2 | 4/2016 | Roninson et al. | |
| 9,370,304 B2 | 6/2016 | Cao et al. | |
| 9,717,808 B2 | 8/2017 | Chiu et al. | |
| 9,754,371 B2 | 9/2017 | Kateb et al. | |
| 10,043,293 B2 * | 8/2018 | Ida | G06T 12/10 |
| 11,526,994 B1 * | 12/2022 | Reyes | G06T 7/174 |
| 11,545,266 B2 * | 1/2023 | Kalafut | G06N 3/04 |
| 11,776,173 B2 * | 10/2023 | Bhushan | G06T 12/30 |
| | | | 382/131 |
| 12,198,333 B2 * | 1/2025 | Kwon | G06T 7/0012 |
| 12,257,063 B2 * | 3/2025 | Simonyan | A61B 5/055 |
| 2002/0083478 A1 | 6/2002 | Sawyers et al. | |
| 2009/0005258 A1 | 1/2009 | Holstege et al. | |
| 2010/0009920 A1 | 1/2010 | Nakamura et al. | |
| 2010/0113297 A1 | 5/2010 | Lidereau et al. | |
| 2011/0150840 A1 | 6/2011 | Moskal et al. | |
| 2015/0110745 A1 | 4/2015 | Solomon et al. | |
| 2015/0265641 A1 | 9/2015 | Glazier | |
| 2017/0020460 A1 | 1/2017 | Leblond et al. | |
| 2017/0274069 A1 | 9/2017 | Ghochikyan et al. | |
| 2019/0252075 A1 | 8/2019 | Schmidt | |
| 2021/0213133 A1 | 7/2021 | Brahmbhatt et al. | |

FOREIGN PATENT DOCUMENTS

| | | |
|---|---|---|
| CN | 102175625 A | 9/2011 |
| CN | 103345638 A | 10/2013 |
| CN | 103793916 A | 5/2014 |
| CN | 102436551 B | 9/2014 |
| CN | 106780515 A | 5/2017 |
| CN | 107067395 A | 8/2017 |
| CN | 107406876 A | 11/2017 |
| CN | 107423756 A | 12/2017 |
| TW | 200920437 A | 5/2009 |
| TW | 201617091 A | 5/2016 |
| TW | 202213382 A | 4/2022 |

* cited by examiner

<u>200</u>

IDENTIFYING AND QUANTIZING SYSTEM, OPERATION METHOD THEREOF, AND NON-TRANSITORY COMPUTER READABLE MEDIUM

RELATED APPLICATIONS

This application claims priority to Taiwan Patent Application No. 112137958, filed Oct. 3, 2023, the entirety of which is herein incorporated by reference.

BACKGROUND

Field of Invention

The present invention relates to systems and operation methods, and more particularly, identifying and quantizing systems and operation methods thereof.

Description of Related Art

Cancer is the first among the top ten causes of death in Taiwan. With the advancement of cancer treatment, the average life expectancy of various cancers has increased significantly. However, while the survival time of patients has been prolonged, brain metastasis of cancer has become the next treatment topics. Due to its special tissue structure, the brain is difficult for various therapeutic drugs to reach, making the brain a breeding ground for cancer to metastasize and survive after it is controlled at the original site. For the development of imaging technology, MRI can provide clear imaging examinations of the brain, so as to detect tiny brain metastases early, and therefore tumors can be treated before they expand through non-pharmacological treatment, such as various three-dimensional targeted radiation or focused ultrasound therapy. In addition to detecting tumors as early as possible, imaging examinations are also very important for evaluating the efficacy and side effects of tumors being treated. During the treatment process, the size and shape of the tumor may change in different ways, and the brain tissue next to the tumor may also produce varying degrees of cerebral edema, causing various side effects. Tracking these brain changes is critical to the effectiveness of treatments.

Effective treatment must be based on good imaging examinations. However, each MRI examination is composed of a large number of two-dimensional images stacked. Whether it is the discovery of lesions or the evaluation of treatment, it requires manual and careful interpretation. The large number of images not only makes it possible to miss small tumors, but also can only roughly estimate the size of brain tumors and edema, but cannot accurately quantify them, making the clinical assessment of treatment targets and side effects potentially inaccurate.

SUMMARY

In one or more various aspects, the present disclosure is directed to identifying and quantizing systems and operation methods thereof.

An embodiment of the present disclosure is related to an identifying and quantizing system. The identifying and quantizing system includes a storage device and a processor. The storage device is configured to store at least one instruction. The processor is coupled to the storage device, and the processor configured to access and execute the at least one instruction for: splitting a T2 weighted image into a first group of two-dimensional images; inputting the first group of two-dimensional images into a mask R-CNN (mask region-based convolutional neural network) model to obtain a first group of two-dimensional parenchymal brain images; using a first group of two-dimensional parenchymal brain images to form a T2 weighted parenchymal brain images; performing a pre-process on the T2 weighted parenchymal brain image to obtain a pre-processed T2 weighted parenchymal brain image; and using a three-dimensional convolutional neural network model to segment and quantize a brain edema area in the pre-processed T2 weighted parenchymal brain image.

In one embodiment of the present disclosure, the processor accesses and executes the at least one instruction for: co-registering a contrast enhanced T1 (T1C) weighted image to the T2 weighted image to obtain a co-registered T1C weighted image; splitting the co-registered T1C weighted image into a second group of two-dimensional images; inputting the second group of two-dimensional images into the mask R-CNN model to obtain a second group of two-dimensional parenchymal brain images; using the second group of two-dimensional parenchymal brain images to form a T1C weighted parenchymal brain image; performing the pre-process on the T1C weighted parenchymal brain image to obtain a pre-processed T1C weighted parenchymal brain image; and using another three-dimensional convolutional neural network model to segment and quantize a metastatic brain tumor area in the pre-processed T1C weighted parenchymal brain image.

In one embodiment of the present disclosure, the pre-process includes an image resampling.

In one embodiment of the present disclosure, the pre-process includes image normalization.

In one embodiment of the present disclosure, the processor accesses and executes the at least one instruction for: pre-training the three-dimensional convolutional neural network model, where the three-dimensional convolutional neural network model has two convolution paths, one of the two convolution paths extracts each region in training data so as to perform a feature extraction on the each region, another of the two convolution paths selects each corresponding expanded area based on a center point of the each area and performs an under-sampling on the each corresponding expanded area for the feature extraction.

Another embodiment of the present disclosure is related to an operation method of an identifying and quantizing system. The operation method includes steps of: splitting a T2 weighted image into a first group of two-dimensional images; inputting the first group of two-dimensional images into a mask R-CNN model to obtain a first group of two-dimensional parenchymal brain images; using a first group of two-dimensional parenchymal brain images to form a T2 weighted parenchymal brain images; performing a pre-process on the T2 weighted parenchymal brain image to obtain a pre-processed T2 weighted parenchymal brain image; and using a three-dimensional convolutional neural network model to segment and quantize a brain edema area in the pre-processed T2 weighted parenchymal brain image.

In one embodiment of the present disclosure, the operation method further comprises: co-registering a T1C weighted image to the T2 weighted image to obtain a co-registered T1C weighted image; splitting the co-registered T1C weighted image into a second group of two-dimensional images; inputting the second group of two-dimensional images into the mask R-CNN model to obtain a second group of two-dimensional parenchymal brain images; using the second group of two-dimensional parenchymal brain images to form a T1C weighted parenchymal brain image; performing the pre-process on the T1C weighted parenchymal brain image to obtain a pre-processed T1C weighted parenchymal brain image; and using another three-dimensional convolutional neural network model to segment and quantize a metastatic brain tumor area in the pre-processed T1C weighted parenchymal brain image.

In one embodiment of the present disclosure, the step of performing the pre-process on the T2 weighted parenchymal brain image includes: performing an image resampling on the T2 weighted parenchymal brain image.

In one embodiment of the present disclosure, the step of performing the pre-process on the T2 weighted parenchymal brain image includes: performing an image normalization on the T2 weighted parenchymal brain image.

In one embodiment of the present disclosure, the operation method further includes: pre-training the three-dimensional convolutional neural network model, where the three-dimensional convolutional neural network model has two convolution paths, one of the two convolution paths extracts each region in training data so as to perform a feature extraction on the each region, another of the two convolution paths selects each corresponding expanded area based on a center point of the each area and performs an under-sampling on the each corresponding expanded area for the feature extraction.

Technical advantages are generally achieved, by embodiments of the present disclosure. With the identifying and quantizing system and its operation method of the present disclosure, the technology of image interpretation and segmentation using artificial intelligence allows computers to automatically segment not only metastatic brain tumors, but also brain edema in adjacent areas. With the assistance of artificial intelligence, clinicians can not only quickly and without omissions find the lesions that need treatment, but also quantitatively analyze the possible brain edema area before and after treatment, thereby improving the accuracy and safety of treatment.

Many of the attendant features will be more readily appreciated, as the same becomes better understood by reference to the following detailed description considered in connection with the accompanying drawings.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
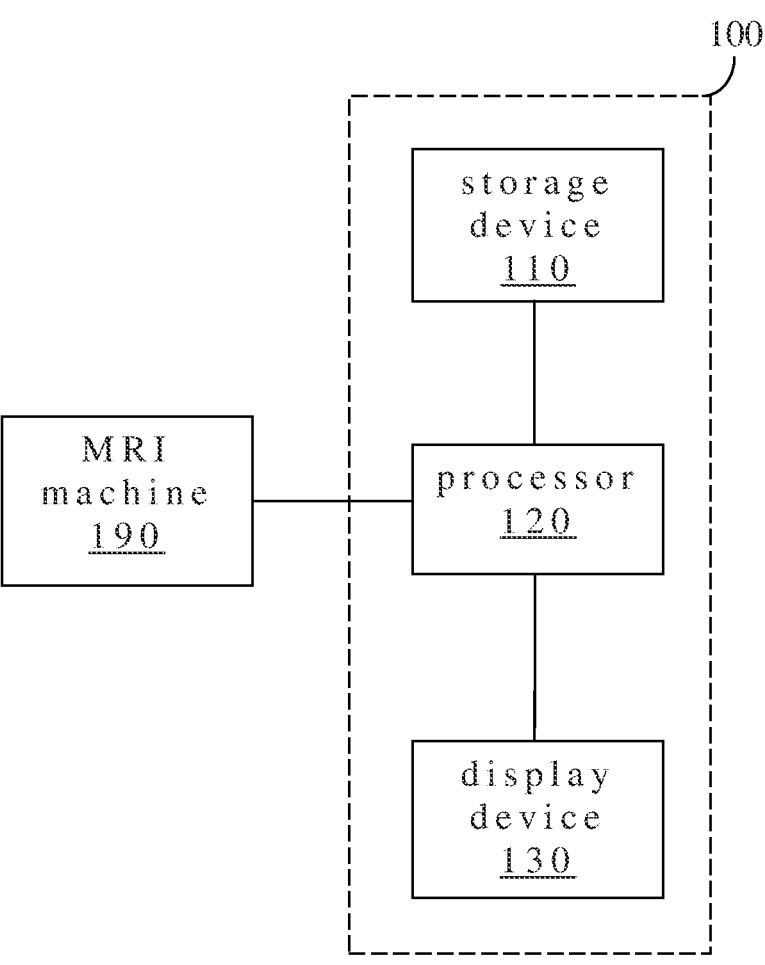
FIG. 1 is a block diagram of an identifying and quantizing system according to one embodiment of the present disclosure.

Reference will now be made in detail to the present embodiments of the invention, examples of which are illustrated in the accompanying drawings. Wherever possible, the same reference numbers are used in the drawings and the description to refer to the same or like parts.

Referring to FIG. 1, in one aspect, the present disclosure is directed to an identifying and quantizing system 100. The identifying and quantizing system 100 may be easily integrated into a computer and may be applicable or readily adaptable to all technologies. Technical advantages are generally achieved by the identifying and quantizing system 100 according to embodiments of the present disclosure. Herewith the identifying and quantizing system 100 is described below with FIG. 1.

The subject disclosure provides the identifying and quantizing system 100 in accordance with the subject technology. Various aspects of the present technology are described with reference to the drawings. In the following description, for purposes of explanation, numerous specific details are set forth in order to provide a thorough understanding of one or more aspects. It can be evident, however, that the present technology can be practiced without these specific details. In other instances, well-known structures and devices are shown in block diagram form in order to facilitate describing these aspects. The word "exemplary" is used herein to mean "serving as an example, instance, or illustration." Any embodiment described herein as "exemplary" is not necessarily to be construed as preferred or advantageous over other embodiments.

In practice, for example, the identifying and quantizing system 100 can be a computer server. The computer server can be remotely managed in a manner that substantially provides accessibility, consistency, and efficiency. Remote management removes the need for input/output interfaces in the servers. An administrator can manage a large data centers containing numerous rack servers using a variety of remote management tools, such as simple terminal connections, remote desktop applications, and software tools used to configure, monitor, and troubleshoot server hardware and software.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about", "substantially" or "approximately" can be inferred if not expressly stated.

In practice, in an embodiment of the present disclosure, the identifying and quantizing system 100 can selectively establish a connection with the MRI (magnetic resonance imaging) machine 190. It should be understood that in the embodiments and the scope of the patent application, the description involving "connection" can generally refer to a component that indirectly communicates with another component by wired and/or wireless communication through another component, or a component that is physically connected to another element without through another element. For example, the identifying and quantizing system 100 can indirectly communicate with the MRI machine 190 through wired and/or wireless communication via another component, or the identifying and quantizing system 100 can be physically connected to the MRI machine 190 without another component. Those with ordinary skill in the art may select the connection manner depending on the desired application.

FIG. 1 is a block diagram of the identifying and quantizing system 100 according to one embodiment of the present disclosure. As shown in FIG. 1, the identifying and quantizing system 100 includes a storage device 110, a processor 120 and a display device 130. For example, the storage device 110 can be a hard drive, a flash memory or another storage device, the processor 120 can be a central processing unit, and the display device 130 can be a built-in display or an external screen.

In structure, the identifying and quantizing system 100 is electrically connected to the MRI machine 190, the storage device 110 is electrically connected to the processor 120, the processor 120 is electrically connected to the display device 130. It should be noted that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. For example, the storage device 110 may be a built-in storage device that is directly connected to the processor 120, or the storage device 110 may be an external storage device that is indirectly connected to the processor 120 through the network device.

In practice, in some embodiments of the present disclosure, the MRI machine 190 collects a plurality of original MRI data from the subject. In practice, for example, the MRI device 190 can capture a T2 weighted image and a contrast enhanced T1 (T1C) weighted image of the patient, and the T1C weighted image can be a T1 weighted image after contrast agent injection and development. Although only one MRI device 190 is shown in FIG. 1, this does not limit the present disclosure. In practice, the MRI device 190 can generally refer to one or more MRI devices. Those with ordinary skill in the art may flexibly select the amount of MRI device(s) depending on the desired application.

In use, the storage device 110 store the weighted image, the T1C weighted image and at least one instruction, and the processor 120 accesses and executes the at least one instruction for: splitting a T2 weighted image into a first group of two-dimensional images; inputting the first group of two-dimensional images into a mask R-CNN (mask region-based convolutional neural network) model to obtain a first group of two-dimensional parenchymal brain images; using a first group of two-dimensional parenchymal brain images to form a T2 weighted parenchymal brain images; performing a pre-process on the T2 weighted parenchymal brain image to obtain a pre-processed T2 weighted parenchymal brain image; and using a three-dimensional convolutional neural network model to segment and quantize a brain edema area in the pre-processed T2 weighted parenchymal brain image. The display device 130 can display the brain edema area in the pre-processed T2 weighted parenchymal brain image. In practice, compared with other images, the processor 120 uses T2 weighted images to perform the above processing, which is more conducive to identify and quantify the brain edema area.

Similarly, in some embodiments of the present disclosure, the processor 120 accesses and executes the at least one instruction for: the processor accesses and executes the at least one instruction for: co-registering a contrast enhanced T1 (T1C) weighted image to the T2 weighted image to obtain a co-registered T1C weighted image; splitting the co-registered T1C weighted image into a second group of two-dimensional images; inputting the second group of two-dimensional images into the mask R-CNN model to obtain a second group of two-dimensional parenchymal brain images; using the second group of two-dimensional parenchymal brain images to form a T1C weighted parenchymal brain image; performing the pre-process on the T1C weighted parenchymal brain image to obtain a pre-processed T1C weighted parenchymal brain image; and using another three-dimensional convolutional neural network model to segment and quantize a metastatic brain tumor area in the pre-processed T1C weighted parenchymal brain image. The display device 130 can display the metastatic brain tumor area in the pre-processed T1C weighted parenchymal brain image. In practice, compared with other images, the processor 120 uses T1C weighted images to perform the above processing, which is more conducive to identify and quantify the metastatic brain tumor areas. In addition, by co-registering the T1C weighted image to the T2 weighted image, the same mask R-CNN model can extract brain masks (i.e., substantial brain images) from the T2 weighted image and/or the co-registered T1C weighted image.

Regarding the above-mentioned Mask R-CNN, it can effectively analyze two-dimensional images to extract brain masks (i.e., substantial brain images). The original MR images include not only the cerebrospinal fluid, cerebrum, and cerebellum, but also the skull, scalp, and non-parenchymal brain regions. The brain edema and tumors to be segmented and quantified by the present disclosure occur in the brain parenchyma area. There are some noises or artifacts produced during magnetic resonance imaging, and some noises or artifacts show higher grayscale values in the T2 weighted image. In order to avoid misjudgment by the neural network and waste of training resources when segmenting cerebral edema, the present disclosure can only extract brain parenchymal areas for segmentation and quantification, excluding non-parenchymal brain areas.

The method of extracting brain masks is to use two-dimensional mask R-CNN. The mask R-CNN can achieve target detection, target classification and pixel-level target segmentation. It is a new convolutional neural network based on the Fast/Faster R-CNN architecture.

The training data for training to extract brain masks is to first use Statistical Parametric Mapping 12 (SPM 12). SPM software is specially designed to analyze brain imaging data. After locating the anterior commissure point in magnetic resonance imaging, the software can segment gray matter, white matter, cerebrospinal fluid, skull and soft tissue. The segmented gray matter, white matter and cerebrospinal fluid are then combined, and the brain mask generated by SPM is further manually repaired. After final inspection by a doctor, these data are used as the gold standard of supervised learning models.

The images used in training the brain extraction model are all T2 weighted images. The T1C weighted image is co-registered to the T2 weighted image to generate a co-registered T1C weighted image. The model segment mask trained through the T2 weighted image can be applied to co-registered T1C weighted image.

There is a total of 40 patients (a total of 1799 slices) in the data set of the brain extraction model, and the number of slices for each patient ranges from 42 to 54, in which 28 slices are the training set, 6 slices are the verification set, and 6 slices are the test set.

Regarding the above pre-process, specifically, in some embodiments of the present disclosure, the pre-process includes an image resampling.

Voxel spacing defines the physical size of each voxel in real situations. Although the size of each person's head is different, the image resolution of magnetic resonance imaging is fixed, which may cause the voxel spacing of each patient's image to be different.

In addition, since the three-dimensional convolutional neural network model (e.g., DeepMedic) model can randomly extract one of the areas of the data during training. In order to avoid that the size of the data extracted each time is different in the real situation to decrease the performance of the model, resampling the voxel spacing of all patients to 1×1×1 mm3 facilitates the learning of convolutional neural networks.

During the resampling process, the dimensions of each axis may change, so interpolation is used to make up for the extra voxels. The present disclosure adopts two interpolation methods: a B-Spline interpolation method and a nearest neighbor interpolation method. The B-Spline interpolation method can be applied to the T2-weighted and T1C-weighted images. The nearest neighbor interpolation method can be applied to the brain edema mask (i.e., the brain edema area).

Then, in one embodiment of the present disclosure, the pre-process includes image normalization.

The MRI data are taken sequentially by The MRI device 190 are different each time, and the gray scale value range of each data is not the same, which easily causes the convolutional neural network to make wrong judgments. The Z-score regularization method is used to rescale the grayscale value of each data within the actual brain range to data with a mean value of 0 and a standard deviation of 1. It enhances the consistency of each piece of data and helps improve the robustness of the model.

The formula defines $z=(x-\mu)/\sigma$, where z is the normalized gray scale value, x is the original gray scale value, u is the average gray scale value, and $\sigma$ is the standard deviation of the gray scale value.

Regarding the way to identify and quantify the brain edema area, In one embodiment of the present disclosure, the processor 120 accesses and executes the at least one instruction for: pre-training the three-dimensional convolutional neural network model, where the three-dimensional convolutional neural network model has two convolution paths, one of the two convolution paths extracts each region in training data so as to perform a feature extraction on the each region, another of the two convolution paths selects each corresponding expanded area (i.e., a larger area than the original area) based on a center point of the each area and performs an under-sampling on the each corresponding expanded area for the feature extraction.

For example, the network architecture for segmenting brain edema and tumors is a three-dimensional convolutional neural network (e.g., DeepMedic), and can accept multiple modalities. It was mentioned in the experiment that a model with good performance can be trained using only a data set of 28 subjects tracked multiple times.

The network architecture used by the three-dimensional convolutional neural network has two convolution paths, one of which is to extract an area in the data to extract features. Another path can expand and select a larger area from the center point of the original area, and perform under-sampling to reduce the resolution, and perform the same feature extraction. In this way, the network will learn the subtler and rougher features of the same area, to improve performance of the edema segmentation.

There is a total of 87 data sets in the segmented brain edema model, including images of patients before and after treatment. Among them, 53 data are used as the training set, 17 data are used as the verification set, and 17 data are used as the test set. And try to put the tracking images of the same patients in the same set to avoid the images in the test set being similar to the images in the training set.

Figure 2:
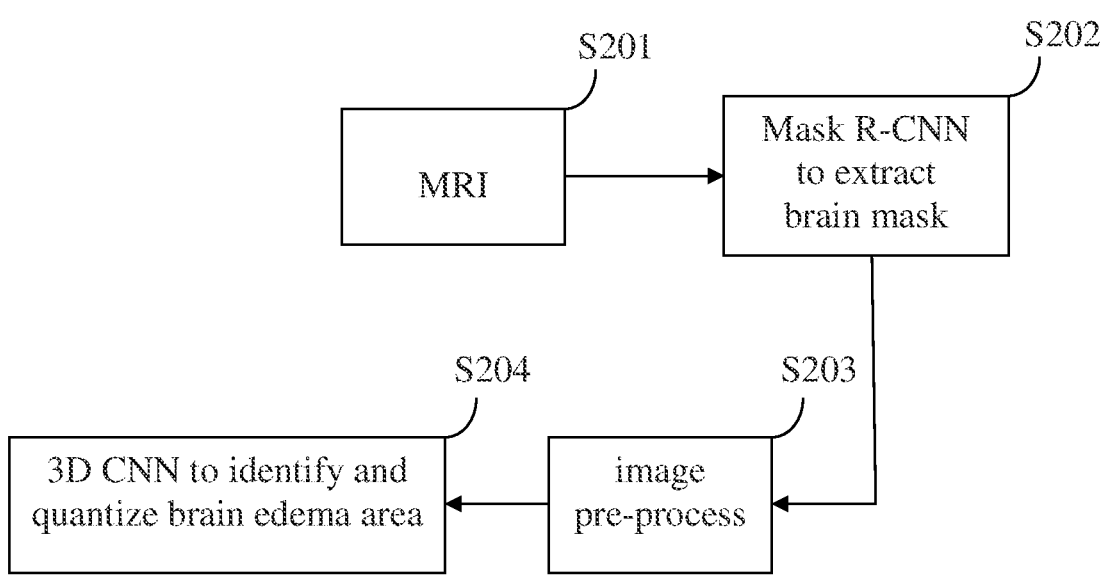
FIG. 2 is a flow chart of an operation method of the identifying and quantizing system according to one embodiment of the present disclosure.

For a more complete understanding of an operation method of the identifying and quantizing system 100, referring FIGS. 1-2, FIG. 2 is a flow chart of the operation method 200 of the identifying and quantizing system 100 according to one embodiment of the present disclosure. As shown in FIG. 2, the operation method 200 includes operations S201-S204. However, as could be appreciated by persons having ordinary skill in the art, for the steps described in the present embodiment, the sequence in which these steps are performed, unless explicitly stated otherwise, can be altered depending on actual needs; in certain cases, all or some of these steps can be performed concurrently.

The operation method 200 may take the form of a computer program product on a computer-readable storage medium having computer-readable instructions embodied in the medium. Any suitable storage medium may be used including non-volatile memory such as read only memory (ROM), programmable read only memory (PROM), erasable programmable read only memory (EPROM), and electrically erasable programmable read only memory (EEPROM) devices; volatile memory such as SRAM, DRAM, and DDR-RAM; optical storage devices such as CD-ROMs and DVD-ROMs; and magnetic storage devices such as hard disk drives and floppy disk drives.

In operation S201, a T2 weighted image is split into a first group of two-dimensional images. In operation S202, the first group of two-dimensional images is inputted into a mask R-CNN model to obtain a first group of two-dimensional parenchymal brain images, and a first group of two-dimensional parenchymal brain images is used to form a T2 weighted parenchymal brain images. In operation S203, a pre-process is performed on the T2 weighted parenchymal brain image to obtain a pre-processed T2 weighted parenchymal brain image. In operation S204, a three-dimensional convolutional neural network model (i.e., a three-dimensional convolutional neural network model trained in advance with a large number of other T2 weighted parenchymal brain images) is used to segment and quantize a brain edema area in the pre-processed T2 weighted parenchymal brain image.

In some embodiments of the present disclosure, in operation S201, a T1C weighted image is co-registered to the T2 weighted image to obtain a co-registered T1C weighted image, and the co-registered T1C weighted image is split into a second group of two-dimensional images; in operation S202, the second group of two-dimensional images is inputted into the mask R-CNN model to obtain a second group of two-dimensional parenchymal brain images, and the second group of two-dimensional parenchymal brain images is used to form a T1C weighted parenchymal brain image; in operation S203, the pre-process is performed on the T1C weighted parenchymal brain image to obtain a pre-processed T1C weighted parenchymal brain image; in operation S204, another three-dimensional convolutional neural network model (i.e., a three-dimensional convolutional neural network model trained in advance with a large number of other T1C weighted parenchymal brain images) is used to segment and quantize a metastatic brain tumor area in the pre-processed T1C weighted parenchymal brain image.

In some embodiments of the present disclosure, in operation S203, the image resampling is performed on the T2 weighted parenchymal brain image.

In some embodiments of the present disclosure, in operation S203, the image normalization is performed on the T2 weighted parenchymal brain image.

Regarding a pre-training method for the three-dimensional convolutional neural network model, in some embodiments of the present disclosure, the operation method 200 further includes: pre-training the three-dimensional convolutional neural network model, where the three-dimensional convolutional neural network model has two convolution paths, one of the two convolution paths extracts each region in training data so as to perform a feature extraction on the each region, another of the two convolution paths selects each corresponding expanded area based on a center point of the each area and performs an under-sampling on the each corresponding expanded area for the feature extraction.

In view of the above, technical advantages are generally achieved, by embodiments of the present disclosure. With the identifying and quantizing system 100 and its operation method 200 of the present disclosure, the technology of image interpretation and segmentation using artificial intelligence allows computers to automatically segment not only metastatic brain tumors, but also brain edema in adjacent areas. With the assistance of artificial intelligence, clinicians can not only quickly and without omissions find the lesions that need treatment, but also quantitatively analyze the possible brain edema area before and after treatment, thereby improving the accuracy and safety of treatment.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An identifying and quantizing system, comprising:

a storage device configured to store at least one instruction; and a processor coupled to the storage device, and the processor configured to access and execute the at least one instruction for:

splitting a T2 weighted image into a first group of two-dimensional images;

inputting the first group of two-dimensional images into a mask R-CNN (mask region-based convolutional neural network) model to obtain a first group of two-dimensional parenchymal brain images;

using a first group of two-dimensional parenchymal brain images to form a T2 weighted parenchymal brain images;

performing a pre-process on the T2 weighted parenchymal brain image to obtain a pre-processed T2 weighted parenchymal brain image;

using a three-dimensional convolutional neural network model to segment and quantize a brain edema area in the pre-processed T2 weighted parenchymal brain image;

co-registering a contrast enhanced T1 (T1C) weighted image to the T2 weighted image to obtain a co-registered T1C weighted image;

splitting the co-registered T1C weighted image into a second group of two-dimensional images;

inputting the second group of two-dimensional images into the mask R-CNN model to obtain a second group of two-dimensional parenchymal brain images;

using the second group of two-dimensional parenchymal brain images to form a T1C weighted parenchymal brain image;

performing the pre-process on the T1C weighted parenchymal brain image to obtain a pre-processed T1C weighted parenchymal brain image; and using another three-dimensional convolutional neural network model to segment and quantize a metastatic brain tumor area in the pre-processed T1C weighted parenchymal brain image.

2. The identifying and quantizing system of claim 1, wherein the pre-process comprises an image resampling.

3. The identifying and quantizing system of claim 1, wherein the pre-process comprises an image normalization.

4. The identifying and quantizing system of claim 1, wherein the processor accesses and executes the at least one instruction for:

pre-training the three-dimensional convolutional neural network model, wherein the three-dimensional convolutional neural network model has two convolution paths, one of the two convolution paths extracts each region in training data so as to perform a feature extraction on the each region, another of the two convolution paths selects each corresponding expanded area based on a center point of the each area and performs an under-sampling on the each corresponding expanded area for the feature extraction.

5. An operation method of an identifying and quantizing system, and the operation method comprising steps of:

splitting a T2 weighted image into a first group of two-dimensional images;

inputting the first group of two-dimensional images into a mask R-CNN model to obtain a first group of two-dimensional parenchymal brain images;

using a first group of two-dimensional parenchymal brain images to form a T2 weighted parenchymal brain images;

performing a pre-process on the T2 weighted parenchymal brain image to obtain a pre-processed T2 weighted parenchymal brain image;

using a three-dimensional convolutional neural network model to segment and quantize a brain edema area in the pre-processed T2 weighted parenchymal brain image;

co-registering a T1C weighted image to the T2 weighted image to obtain a co-registered T1C weighted image;

splitting the co-registered T1C weighted image into a second group of two-dimensional images;

inputting the second group of two-dimensional images into the mask R-CNN model to obtain a second group of two-dimensional parenchymal brain images;

using the second group of two-dimensional parenchymal brain images to form a T1C weighted parenchymal brain image;

performing the pre-process on the T1C weighted parenchymal brain image to obtain a pre-processed T1C weighted parenchymal brain image; and using another three-dimensional convolutional neural network model to segment and quantize a metastatic brain tumor area in the pre-processed T1C weighted parenchymal brain image.

6. The operation method of claim 5, wherein the step of performing the pre-process on the T2 weighted parenchymal brain image comprises:

performing an image resampling on the T2 weighted parenchymal brain image.

7. The operation method of claim 5, wherein the step of performing the pre-process on the T2 weighted parenchymal brain image comprises:

performing an image normalization on the T2 weighted parenchymal brain image.

8. The operation method of claim 5, further comprising:

pre-training the three-dimensional convolutional neural network model, wherein the three-dimensional convolutional neural network model has two convolution paths, one of the two convolution paths extracts each region in training data so as to perform a feature extraction on the each region, another of the two convolution paths selects each corresponding expanded area based on a center point of the each area and performs an under-sampling on the each corresponding expanded area for the feature extraction.

9. A non-transitory computer readable medium to store a plurality of instructions for commanding a computer to execute an operation method, and the operation method comprising steps of:

splitting a T2 weighted image into a first group of two-dimensional images;

inputting the first group of two-dimensional images into a mask R-CNN model to obtain a first group of two-dimensional parenchymal brain images;

using a first group of two-dimensional parenchymal brain images to form a T2 weighted parenchymal brain images;

performing a pre-process on the T2 weighted parenchymal brain image to obtain a pre-processed T2 weighted parenchymal brain image;

using a three-dimensional convolutional neural network model to segment and quantize a brain edema area in the pre-processed T2 weighted parenchymal brain image;

co-registering a T1C weighted image to the T2 weighted image to obtain a co-registered T1C weighted image;

splitting the co-registered T1C weighted image into a second group of two-dimensional images;

inputting the second group of two-dimensional images into the mask R-CNN model to obtain a second group of two-dimensional parenchymal brain images;

using the second group of two-dimensional parenchymal brain images to form a T1C weighted parenchymal brain image;

performing the pre-process on the T1C weighted parenchymal brain image to obtain a pre-processed T1C weighted parenchymal brain image; and using another three-dimensional convolutional neural network model to segment and quantize a metastatic brain tumor area in the pre-processed T1C weighted parenchymal brain image.

10. The non-transitory computer readable medium of claim 9, wherein the step of performing the pre-process on the T2 weighted parenchymal brain image comprises:

performing an image resampling on the T2 weighted parenchymal brain image.

11. The non-transitory computer readable medium of claim 9, wherein the step of performing the pre-process on the T2 weighted parenchymal brain image comprises:

performing an image normalization on the T2 weighted parenchymal brain image.

12. The non-transitory computer readable medium of claim 9, wherein the operation method further comprises:

pre-training the three-dimensional convolutional neural network model, wherein the three-dimensional convolutional neural network model has two convolution paths, one of the two convolution paths extracts each region in training data so as to perform a feature extraction on the each region, another of the two convolution paths selects each corresponding expanded area based on a center point of the each area and performs an under-sampling on the each corresponding expanded area for the feature extraction.

* * * * *